United States Patent [19]
Liu

[11] Patent Number: 5,294,325
[45] Date of Patent: Mar. 15, 1994

[54] MINIATURIZED FLUID CONVEYING DEVICE AND METHODS OF USE THEREOF

[75] Inventor: Su Y. Liu, Sarasota, Fla.

[73] Assignee: World Precision Instruments, Inc., Sarasota, Fla.

[21] Appl. No.: 911,156

[22] Filed: Jul. 9, 1992

[51] Int. Cl.⁵ .......................................... G01N 27/26
[52] U.S. Cl. .................................... 204/418; 204/416;
128/763; 128/768; 128/772; 604/190; 604/191;
604/239; 604/272; 604/280; 606/181
[58] Field of Search ....................... 128/763, 768, 772;
606/181, 190; 604/191, 239, 272, 280, 5;
204/416, 418, 419

[56] References Cited

U.S. PATENT DOCUMENTS

| | | | |
|---|---|---|---|
| 4,453,927 | 6/1984 | Sinko | 604/190 |
| 5,061,237 | 10/1991 | Gessler et al. | 604/5 |

FOREIGN PATENT DOCUMENTS 271775 12/1987 European Pat. Off. ............ 604/239

*Primary Examiner*—John Niebling
*Assistant Examiner*—Bruce F. Bell
*Attorney, Agent, or Firm*—Chilton, Alix & Van Kirk

[57] ABSTRACT

Small quantities of liquid are conveyed, either for the purpose of filling micropipettes or to function as an electrolyte in an ion selective electrode, in a flexible non-metallic capillary tube which is mounted, at a first end, in an adapter fitting. The fitting defines a socket for coupling to a source of liquid, a hypodermic syringe for example, or for receiving an electrochemical half-cell which will contact an electrolyte in the tube. A filter may be interposed between the fitting and hypodermic syringe so as to frictionally engage both when the device is employed for filling micropipettes.

17 Claims, 2 Drawing Sheets

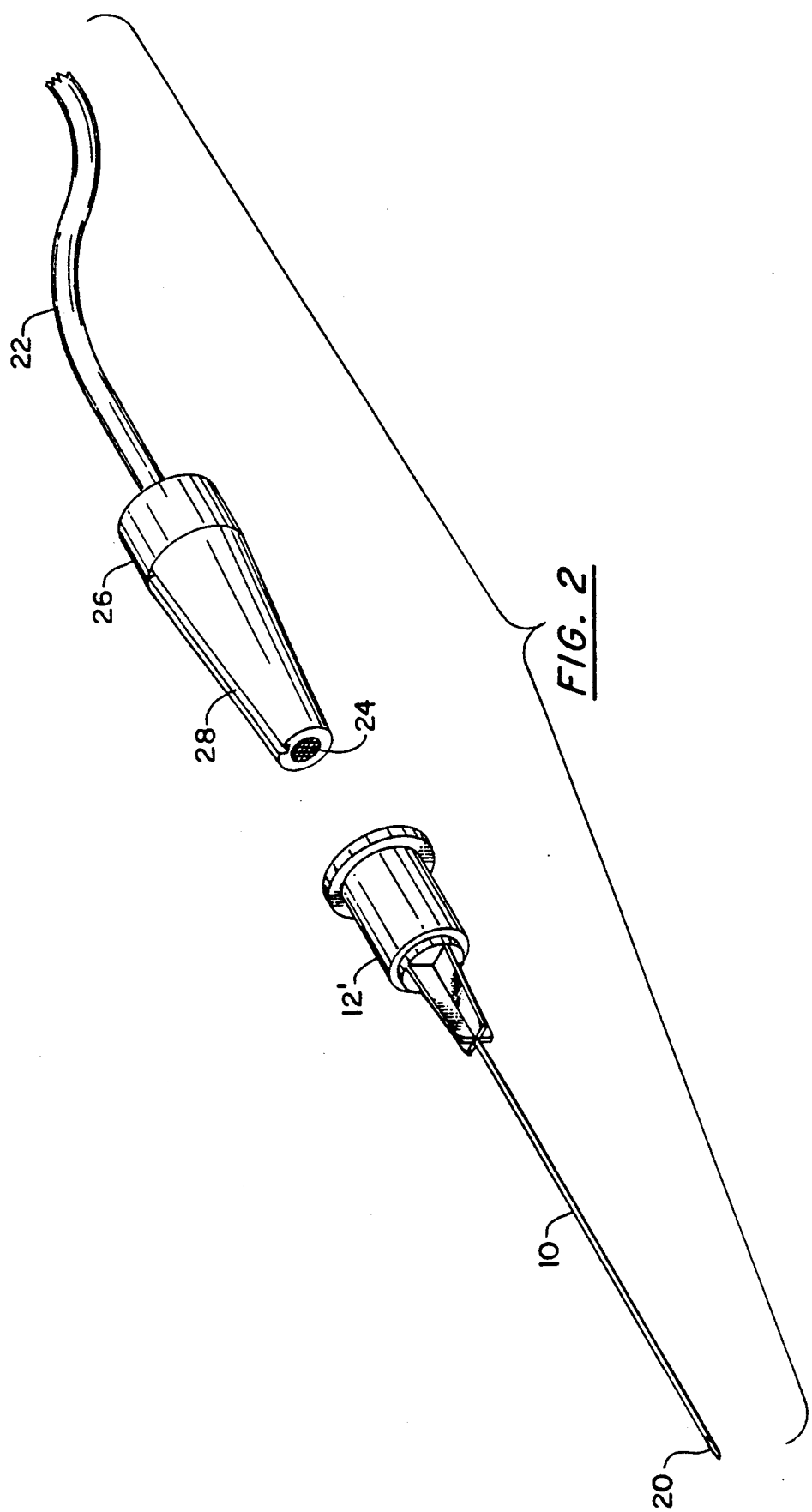

MINIATURIZED FLUID CONVEYING DEVICE AND METHODS OF USE THEREOF

BACKGROUND OF THE INVENTION

1. Field of the Invention

The present invention relates to miniaturized apparatus for conveying small quantities of liquid and particularly to fluid filling devices and miniaturized electrodes. More specifically, this invention is directed to techniques for conveying minute quantities of liquids and especially for techniques for filling small capillary tube micropipettes and other tiny chambers or vessels with a liquid. Accordingly, the general objects of the present invention are to provide novel and improved devices and methods of such character.

2. Description of the Prior Art

While not limited thereto in its utility, as will become apparent from the discussion below, the present invention is particularly useful in the filling of small capillary tube micropipettes and other small volume chambers or vessels that are normally difficult to fill completely with fluid because of narrow, deep or convoluted fluid passageways. Micropipettes, usually fabricated from glass and having microscopically small tips, find widespread usage in biological and chemical research for injecting fluid material into living cells and organelles in order, for example, to permit measurement of the electrical properties of such cells. Micropipettes are also employed to deliver minute amounts of fluid for microchemical analysis. The filling of micropipettes with the fluid material to be injected without the inclusion of air bubbles and dust particles is a problem of long standing in the art. The clogging of the micropipette tip by particles present in the injecting solution is one of the major causes of failure in microinjection experiments.

The technique for filling micropipettes most commonly employed prior to the present invention involves the use of a long, stainless steel hypodermic needle. However, the KCl solution used in the filling process can corrode and plug such stainless steel needles within a few days if the needle is not thoroughly cleaned after each use. Further, for micropipettes which are used in the study of ion channels, e.g., patch pipettes, the use of a metallic needle to fill the micropipette may have the undesirable result of introduction of metal ions into the filling solution. It is also to be noted that, when a metal needle is filled with a solution containing EDTA or EGTA, the solution can become very acidic within several minutes because EDTA chelates metal ions from the needle and therefore releases protons into the solution.

To summarize, there has been a long standing need in the art for a method of and apparatus for filling micropipettes easily and reliably. A filling technique and apparatus which meets the requirements of the art must eliminate air bubble formation and clogging due to the washing down of dust particles. The filling apparatus must also be nonmetallic, be reasonably durable and be sufficiently stiff to not bend significantly under its own weight while at the same time having enough flexibility to insure against easy fracture.

Filling apparatus in accordance with the present invention also has utility as a microelectrode and particularly an ion selective microelectrode. Such electrodes contain a liquid electrolyte selected as a function of the intended application. The same problems associated with the filling of micropipettes, as discussed above, are encountered when attempting to fill a microelectrode with an electrolyte. These problems have previously not been solved in a manner which is conducive to the efficient production of microelectrodes having a long service life.

SUMMARY OF THE INVENTION

The present invention overcomes the above-discussed and other deficiencies and disadvantages of the prior art by providing a novel and improved method for conveying minute quantities of liquid and devices for use in the practice of such method. The invention also encompasses the employment of such method and devices to provide a novel microelectrode. The invention is predicated upon the use of a plastic coated, non-metallic capillary tube and particularly a glass or ceramic tube clad with a polymer which allows a degree of bending of the tube without fracture. The coated tube is mounted, at a first end, in a fitting designed to engage a source of fluid. In accordance with a preferred embodiment, wherein the invention is employed to fill micropipettes, the fluid source may be a syringe coupled to a filter which, in turn, frictionally engages the fitting. The tube, fitting, filter and syringe thus cooperate to define a liquid conveying device which may be inserted into a micropipette which is to be filled.

When employed as a microelectrode, an electrochemical half-cell is supporting in the fitting so as to be in contact with an electrolyte which has been injected into the tube. The electrolyte is captured in the tube by formation of an ion selective membrane over the end of the tube which is displaced from the fitting.

BRIEF DESCRIPTION OF THE DRAWINGS

The present invention may be better understood and its numerous objects and advantages will become apparent to those skilled in the art by reference to the accompanying drawings wherein like reference numerals refer to like elements in the Figures and in which:

FIG. 2 is an exploded perspective view of an ion selective microelectrode in accordance with the present invention.

DESCRIPTION OF THE DISCLOSED EMBODIMENTS

Figure 1:
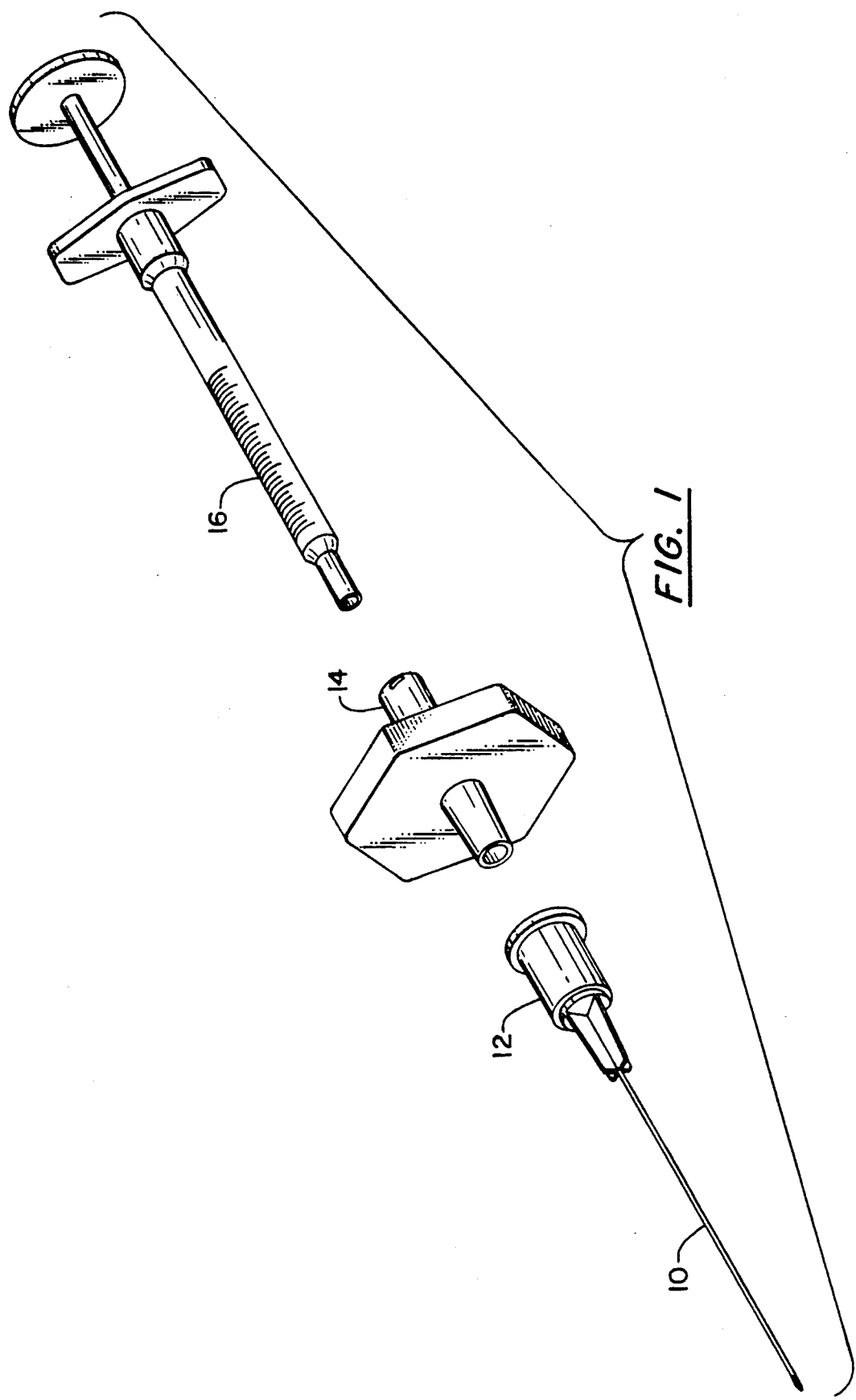
FIG. 1 is an exploded perspective view of a device for use in the filling of micropipettes in accordance with the present invention.

Referring to FIG. 1, the invention employs a plastic coated miniature tube 10 comprised of a non-metallic material. Very fine glass or fused silica tubing, which is normally fragile and breakable, becomes strong and able to bend easily without breaking when provided with a polymer coating and thus is particularly useful in the practice of the present invention. Such plastic coated miniature tubing is available, for example, from Polymicro Technologies, Inc. of Phoenix, Ariz. in the form of polyimide coated fused silica capillary tubing with an inside diameter of as small as two microns. In the assembly of the apparatus of FIG. 1, the small bore, plastic clad, non-metallic tubing 10 is cut to a desired length and either adhesively bonded to or molded into the tip of a fitting 12. Fitting 12 may be comprised of metal or plastic; and, in the disclosed embodiment, is a plastic luer tapered fitting.

The miniature fluid filling device of FIG. 1 also preferably includes a filter 14 included as part of an intermediate member which, at one end, has a taper for engagement with fitting 12. The filter 14, at its opposite side, is provided with a tapered receptacle which is engaged by a hypodermic syringe 16. Thus, in the disclosed embodiment, assembly of the fluid filling device is accomplished simply by inserting a pair of tubular members in tapered conduits respectively defined by fitting 12 and the receptacle of filter 14.

In use of the apparatus of FIG. 1, the syringe 16 is filled with the desired fluid. The syringe is then inserted into the tapered receptacle on filter 14. The combination of syringe and filter is then inserted into fitting 12 with its attached capillary tube. If the device is to be employed to fill a micropipette, the capillary tube 10 is advanced into the pipette until it bottoms at the inside of the pipette tip. Fluid is then forced from the syringe through the filter and into the pipette. Filling from the inside of the pipette, close to the pipette tip, prevents the formation of air bubbles in the lumen of the pipette which is a common problem encountered when using other micropipette filling methods. Also, the filling technique of the present invention will result in dust and other particulate matter floating to the top of the pipette shank and thus not blocking the pipette tip.

It is to be noted that a further advantage to the use of the plastic coated small bore glass or fused silica capillary tubing 10 is that the tubing material is both flexible and chemically inert. Thus, in contrast to the prior art use of relatively inflexible metal syringe needles, the present invention is free of the problems of corrosion or dissolution of small amounts of metal ions into the fluid being conveyed. The present invention also avoids problems, such as are incident to the use of fine plastic fibers as fluid filling devices, associated with too high a degree of flexibility, i.e., fiber limpness.

Referring now to FIG. 2, the device of FIG. 1 may with modification be employed as an ion selective microelectrode. A typical example of an ion selective electrode is the well-known and widely used glass pH electrode. Such electrodes operate on the principle that a thin glass bulb, containing an internal fluid electrolyte and reference electrode, is selectively sensitive to hydrogen ions. Thus, when placed in various solutions containing such ions, the electrode assumes a potential relative to a second reference electrode which obeys the classical Nernst equation. Many other similar devices have been successfully used, for example, to measure selectively the concentration of specific ions such as $Na+$, $K+$, $Ca++$ and $Cl-$ dissolved in solutions of varying ionic composition. While pH electrodes usually employ glass membranes, ion selective electrodes can be made using polymer membranes doped with an ionophore which causes the membranes to be sensitive to particular ions in solutions.

In accordance with the present invention, a liquid mixture of polyvinyl chloride (PVC), a solvent, a plasticizer and a small amount of an ionophore are mixed in appropriate proportions. For example, a mixture comprising, by weight, 65% plasticizer, 34% PVC, 1% ionophore plus enough solvent to liquefy the mixture can be utilized. The tip of the hollow bore glass or fused silica tubing discussed above in the description of FIG. 1 is dipped first into a solution of, for example, dimethyldichlorosilane. The tubing is then heated gently until dry. This procedure assures that the inner bore of the tubing will allow the liquid polymer mixture to adhere. The tip of the silane-treated capillary tube is then dipped into the liquefied PVC mixture. A small amount of the liquid mixture will enter the tubing because of capillary action. The liquid which enters the tubing is allowed to dry thus producing a thin ion selective membrane 20 which seals the tip of the capillary tube 10.

In order to employ the tubing with the membrane 20 as an ion sensor, the tubing must be filled with an electrolyte. For this purpose, a filling device of the type shown in FIG. 1 with a capillary small enough to be inserted inside the capillary of FIG. 2 can be used. The filling device is filled with the appropriate electrolyte. For example, if the membrane is $K+$ sensitive, an electrolyte of potassium chloride solution would be appropriate. If the membrane is to be sensitive to $Na+$, the appropriate filling electrolyte would be a solution containing sodium chloride. Similarly, the filling solution for different membranes should contain chloride salt solutions containing the ion for which the electrode is selective. If the electrode is to be sensitive to a negative ion (anion), a salt containing the anion that the membrane will be sensing should be used in addition to chloride salt in the filling solution.

In order to complete the sensor electrode, the internal electrolyte is connected to an output conductor 22 via an electrochemical half-cell 24 comprised of a silver - silver chloride pellet which has been encapsulated in a tapered, non-metallic plug 26. The tapered plug 26 fits tightly into an identically tapered female fitting 12' which may be same as or similar to the fitting 12 of the FIG. 1 embodiment. Excess fitting electrolyte will be vented to the outside of the electrode by means of a groove 28 which is milled into the side of the plug 26. When assembled, there will be an electrical connection established between the electrolyte in the capillary tubing 10 and the output conductor 22 via the pellet 24. Construction of the silver - silver chloride pellet 24 is described in U.S. Pat. No. 3,137,291.

Tests have shown that an electrode as shown in FIG. 2, manufactured as described above, will respond to changes in ion concentration in a few seconds and will exhibit stable potentials relative to a standard reference electrode placed in the same sample solution.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. Apparatus for transferring a minute quantity of liquid to a small receptacle comprising:
    a flexible non-metallic capillary tube, said tube being comprised of a material selected from glass or a ceramic and having an external coating of a polymer; and
    adaptor means affixed to a first end of said tube, said adaptor means establishing fluid communication between the interior of said tube and a source of liquid, said adaptor means defining a socket for coupling to a source of liquid.

2. The apparatus of claim 1 wherein said polymer is a polyimide.

3. The apparatus of claim 2 wherein said ceramic material comprises fused silica.

4. The apparatus of claim 2 wherein the receptacle is a micropipette and wherein said apparatus further comprises:
    means for establishing a pressure differential across said tube to cause the liquid transfer.

5. The apparatus of claim 2 further comprising:
a syringe; and
means for coupling said syringe to said adapter means socket whereby liquid from within said syringe may be transferred into said tube under the influence of an applied hydraulic pressure.

6. The apparatus of claim 5 wherein said coupling means comprises:
filter means, said filter means having a first connector for establishing a fluid-tight connection with said syringe and a second connector for establishing a fluid-tight connection with said adaptor means socket.

7. The apparatus of claim 12 wherein said adaptor means is a luer fitting which defines a tapered socket.

8. The apparatus of claim 5 wherein said adaptor means is a luer fitting which defines a tapered socket.

9. The apparatus of claim 5 wherein said coupling means comprises:
filter means, said filter means having a first connector for establishing a fluid-tight connection with said syringe and a second connector for establishing a fluid-tight connection with said adaptor means socket.

10. The apparatus of claim 9 wherein said adaptor means is a luer fitting having a tapered socket.

11. An ion sensitive microelectrode comprising:
a flexible nonmetallic capillary tube, said tube being comprised of a material selected from glass or a ceramic and having an external coating of a polymer
an ion selective membrane sealing the bore of said capillary tube at a first end thereof;
an electrolyte filling the bore of said capillary tube;
an output electrical conductor; and
means establishing an electrical connection between said electrolyte and said conductor.

12. The electrode of claim 11 wherein said means establishing an electrical connection comprises: an electrochemical half-cell.

13. The electrode of claim 11 wherein said membrane is comprised of a polymer and wherein said electrolyte is selected as a function of the ion to be detected.

14. The electrode of claim 12 wherein said membrane is comprised of a polymer and wherein said electrolyte is selected as a function of the ion to be detected.

15. The electrode of claim 14 wherein said means establishing an electrical connection further comprises:
an adaptor affixed t the second end of said capillary tube, said adapter having a tapered socket and establishing fluid communication between the bore of said capillary tube and said socket; and
a tapered plug, said plug being complimentary in shape to said socket, said half-cell comprising a body mounted in said plug so as to contact the said electrolyte; said conductor extending into said plug to said body.

16. The electrode of claim 15 wherein said body is a silver/silver chloride pellet.

17. An electrode comprising:
a generally frusto-conically shaped plug comprised of a non-conductive material;
a silver/silver chloride pellet mounted in said plug, a portion of said pellet being exposed at the small diameter end of said plug; and
an electrical conductor extending generally axially of said plug from said pellet to the large diameter end of said plug.

* * * * *

UNITED STATES PATENT AND TRADEMARK OFFICE
CERTIFICATE OF CORRECTION

PATENT NO. : 5,294,325
DATED : March 15, 1994
INVENTOR(S) : Su Y. Liu

It is certified that error appears in the above-indentified patent and that said Letters Patent is hereby corrected as shown below:

In column 5, line 14, "12" should be --2--.

In column 5, line 32, insert a semicolon at the end of the line.

In column 6, line 15, "t" should be --to--.

Signed and Sealed this

Fifth Day of September, 1995

Attest:

BRUCE LEHMAN

*Attesting Officer*  *Commissioner of Patents and Trademarks*